US00PP26121P3

(12) United States Plant Patent
Cain

(10) Patent No.: US PP26,121 P3
(45) Date of Patent: Nov. 24, 2015

(54) GRAPEVINE 'IFG NINETEEN'

(50) Latin Name: ***Vitis Interspecific* hybrid**
Varietal Denomination: IFG Nineteen

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 101 days.

(21) Appl. No.: 13/999,693

(22) Filed: Mar. 18, 2014

(65) Prior Publication Data

US 2015/0271973 P1 Sep. 24, 2015

(51) Int. Cl.
*A01H 5/00* (2006.01)

(52) U.S. Cl.
USPC ..... Plt./205

(58) Field of Classification Search
USPC ..... Plt./205
See application file for complete search history.

*Primary Examiner* — Annette Para

(57) ABSTRACT

This invention is a new and distinct grapevine variety denominated 'IFG Nineteen'. The new grapevine is characterized by producing naturally large seedless red berries having a broad ellipsoid shape with a unique strong fruity flavor having a combination of muscat and labrusca flavors.

1 Drawing Sheet

Latin name of the genus and species claimed: *Vitis Interspecific* hybrid.

Variety denomination: 'IFG Nineteen'.

BACKGROUND OF THE INVENTION

The new and distinct grapevine described and claimed herein originated from a hand pollinated cross of the Princess variety (USDA non-patented) and the A2798 (unnamed interspecific selection from the University of Arkansas) hybridized in May 2006. The abortive seed traces were subsequently embryo cultured and the resulting population of plants was planted in the field in April 2007. The present variety of grapevine was selected as a single plant in September 2008 and was first asexually propagated by hardwood cuttings in December 2008 near Delano, Kern County, Calif. The resulting propagules were planted during April 2009 near Delano, Kern County, Calif. and were found to reproduce true-to-type through at least two generations of asexual reproduction.

BRIEF SUMMARY OF THE INVENTION

The new grapevine 'IFG Nineteen' is characterized by producing naturally large seedless red berries having a broad ellipsoid shape with a unique strong fruity flavor having a combination of muscat and labrusca. Fruits normally ripen mid to late season about early to mid-September near Delano Calif. Fruits are fairly low in acidity, with medium dense firm texture, occasionally noticeable seed traces and are difficult to color in hot climatic conditions. Attachment of the berry to the pedicel is somewhat weak. Vines are very productive and can be pruned to short spurs. The new grapevine differs from its maternal parent the Princess variety by having light red rather than light green berries and by having a very strong fruity muscat and labrusca type flavor as opposed to the mild muscat flavor of the Princess variety. 'IFG Nineteen' can be distinguished from its pollen parent, A2798, by its light red color as opposed to black color, by having larger berry size and by having a combination of muscat and labrusca flavor rather than just a strong labrusca flavor of the A2798.

The interspecific nature of the vine is very evident. Vines are very vigorous with a more erect-horizontal growth habit and very large leaves as compared to typical seedless grapes of the *Vitis vinifera* species.

Grape breeders have used several native American grape species to improve hardiness, disease and insect resistance as well as incorporate aromatic flavors into the *vinifera* species. Previously introduced interspecific varieties have had very limited commercial success due to small fruit size, large seed traces, slipskin texture or lack of firmness. The new grapevine variety is being introduced because of its unique combination of muscat and labrusca flavor combined with firm texture, seedlessness, good adhesion of skin and flesh and naturally large berry size.

BRIEF DESCRIPTION OF THE FIGURE

The accompanying photographic illustration in FIG. 1 illustrates in full color 'IFG Nineteen'. The photograph was taken outdoors with indirect lighting. The colors are as nearly true as is reasonably possible in a color representation of this type.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

Throughout this specification subjective description values conform to those set forth by the International Plant Genetic Resources Institute publication 'Descriptors for Grape' (*vitis* spp.) (1983) which was developed in collaboration with the Office International de la Vigne et du Vin (OIV) and the International Union for the Protection of New Varieties of Plants (UPOV).

The descriptive matter which follows pertains to 'IFG Nineteen' plants grown in the vicinity of Delano, Kern County, Calif. during 2012, and is believed to apply to plants of the variety grown under similar conditions of soil and climate elsewhere:

Vine

General:
- *Size*.—Large.
- *Vigor*.—Very Vigorous.
- *Density of foliage*.—Dense.
- *Productivity*.—Very productive.
- *Root stock*.—Own root.
- *Training method*.—Typically spur pruned leaving 2 bud spurs.

Trunk:
- *Trunk diameter of* 4-*year-old vines at* 30 *cm above the soil line*.—4.6 cm.
- *Shape*.—Medium.
- *Straps*.—Short — split.
- *Surface texture*.—Medium to shaggy.
- *Inner bark color*.—Can be any of the following colors; 165 A and C.

Shoots

Young shoot:
- *Form of tip*.—Wide open.
- *Distribution of anthocyanin coloration of tip*.—Absent.
- *Intensity of anthocyanin coloration of tip*.—Absent.
- *Density of prostrate hairs of tip*.—Dense.
- *Density of erect hairs of tip*.—Absent.
- *Color*.—Yellow-green; can be any of the following colors; 144A, and 146B and C.

Woody shoot (mature canes):
- *Shape*.—Stocky.
- *Internode length*.—Medium; About 8.1 cm.
- *Width at node*.—About 0.9 cm.
- *Cross section*.—Elliptic.
- *Surface*.—Striate.
- *Main color*.—Can be any of the following colors; Greyed orange; 166 A and D.
- *Density of erect hairs of nodes*.—None.
- *Density of erect hairs on internodes*.—None.
- *Growth of axillary shoots*.—Weak, Approximately 7.4 cm.

Flowering shoot:
- *Vigor during flowering*.—Very strong.
- *Attitude during flowering on shoots not tied*.—Horizontal.
- *Color*.—Dorsal side of internodes — Green with Red stripes.
- *Color*.—Ventral side of internodes — Green.
- *Color*.—Dorsal side of nodes — Green with Red stripes.
- *Color*.—Ventral side of nodes — Mostly green but occasionally green with red stripes.
- *Density of prostrate hairs of nodes*.—Sparse.
- *Density of erect hairs of nodes*.—None.
- *Density of prostrate hairs on internode*.—Sparse.
- *Density of erect hairs on internode*.—None.
- *Anthocyanin coloration of buds*.—Absent.

Tendrils:
- *Distribution on the shoot* (*at full flowering*).—Discontinuous.
- *Length of tendril*.—Medium to Long; About 26 cm.
- *Thickness*.—Medium.
- *Color*.—Yellow-Green; can be any of the following colors; 146C, and N144A and B.
- *Form*.—Trifurcated.
- *Number of consecutive tendrils*.—2.

Leaves

Young leaves:
- *Color of upper surface of first four distal unfolded leaves*.—Green.
- *Average intensity of anthocyanin coloration of six distal leaves prior to flowering*.—Absent.
- *Density of prostrate hairs between veins* (*lower surface*).—Dense.
- *Density of prostrate hairs on veins* (*lower surface*).—Dense.
- *Density of erect hairs between veins* (*lower surface*).—Absent.
- *Density of erect hairs on veins* (*lower surface*).—Very sparse.

Mature leaves:
- *Average length*.—About 17.6 cm.
- *Average width*.—About 21.7 cm.
- *Mature leaf size*.—Large to Very large.
- *Shape of blade*.—Pentagonal.
- *Number of lobes*.—5.
- *Anthocyanin coloration of main veins on upper side of blade*.—Weak to Medium.
- *Mature leaf profile*.—Undulate.
- *Blistering surface of blade upper surface*.—Weak.
- *Leaf blade tip*.—In the plane of the leaf.
- *Undulation of margin*.—Medium.
- *Thickness*.—Thick.
- *Undulation of blade between main and lateral veins*.—Overall.
- *Shape of teeth*.—Mixture of both sides straight and both sides convex.
- *Length of teeth*.—Medium.
- *Ratio length/width of teeth*.—Medium.
- *Shape of upper lateral sinuses*.—Open.
- *Depth of upper lateral sinuses*.—Shallow.
- *General shape petiole sinus*.—Half open.
- *Shape of base of upper leaf sinuses*.—U-shaped.
- *Tooth at petiole sinus*.—Absent.
- *Density of prostrate hairs between veins on lower surface of blade*.—Medium.
- *Density if erect hairs between veins on lower surface of blade*.—Absent.
- *Density of prostrate hairs on main veins on lower surface of blade*.—Medium to Dense.
- *Density of erect hairs on main veins on lower surface of blade*.—Sparse.
- *Density of prostrate hairs on main veins on upper surface of blade*.—Sparse.
- *Density of erect hairs on main veins on upper surface of blade*.—None.
- *Autumn coloration of leaves*.—Leaves can be a single color or combination of colors, in a mottled pattern or on the edges of the leaves; Yellow; 11A and B and 12A, and Greyed Orange; 165A and B.

Upper surface:
- *Color*.—Can be any of the following colors; 137B and C, and 138A.
- *Anthocyanin coloration of main veins*.—Absent.

*Surface appearance*.—Semi-glossy.
*Blistering surface of blade*.—Medium.

Lower surface:
*Color*.—Can be any of the following colors; 138A and B and 137C.
*Anthocyanin coloration of main veins* (*lower surface*).—Absent.
*Glossiness*.—Weak.
*Surface texture*.—Smooth.
*Surface appearance*.—Dull.

Petiole:
*Length*.—About 16.7 cm.
*Length of petiole compared to middle vein*.—Slightly shorter.
*Density of prostrate hairs on petiole*.—None.
*Density of erect hairs on petiole*.—None.

Buds:
*Bud fruitfulness*.—Basal: Mostly fruitful.
*Position of first fruitful shoot on previous season cane*.—$1^{st}$ to $2^{nd}$ node.
*Time of bud burst*.—Midseason; about Mar. 15, 2012.

Flowers

General:
*Flower sex*.—Hermaphrodite.
*Length of first inflorescence*.—Medium; About 17.2 cm long by 7.3 cm wide.
*Position of first flowering and fruiting node*.—$3^{rd}$ to $4^{th}$ node (current season growth).
*Number of inflorescence per flowering shoot*.—1.1 to 2.
*Time of bloom*.—Midseason as compared with similar varieties in the growing area of Delano, Calif.
*Date of full bloom*.—May 14, 2012.

Fruit

General:
*Ripening period*.—Midseason to late season; Approximately Sep. 16, 2012.
*Use*.—Fresh market.
*Keeping quality*.—Good.
*Resistance to*.—Insects: Average — not especially resistant or susceptible. Diseases: Average — not especially resistant or susceptible.
*Refractometer test*.—Soluble solids: About 21.6 Brix.
*Brix/acid*.—About 55.4.
*Titratable acidity*.—About 0.39%.
*Juice pH*.—About 3.93.

Cluster:
*Mature cluster length* (*peduncle excluded*).—About 25.2 cm.
*Mature cluster width*.—About 17.2 cm.
*Mature cluster weight*.—About 1058 g.
*Bunch density*.—Medium.
*Number of berries*.—About 174.
*Form*.—Conical.

Peduncle:
*Lignification of peduncle*.—Weak.
*Length of peduncle*.—Medium. Approximately 3.4 cm.

Berry:
*Uniformity of size*.—Uniform.
*Single berry weight*.—About 7.5 g natural; to about 9.2 g when treated with gibberellic acid.
*Shape*.—Broad ellipsoid.
*Seeds*.—Seed traces occasionally noticeable.
*Cross section*.—Circular.
*Berry dimensions*.—Longitudinal axis: About 2.6 cm. horizontal axis: About 2.1 cm.
*Berry firmness*.—Medium firm.
*Particular flavor*.—Muscat combined with Labrusca.
*Bloom* (*cuticular wax*).—Medium.
*Berry separation from pedicel*.—Medium.
*Skin color* (*without bloom*).—Can be any of the following colors; Red-purple; 59 A and B.

Skin:
*Thickness*.—Medium.
*Texture*.—Medium tough.
*Reticulation*.—Absent.
*Tenacity*.—Tenacious to flesh.

What is claimed:

1. A new and distinct variety of grapevine as herein illustrated and described.

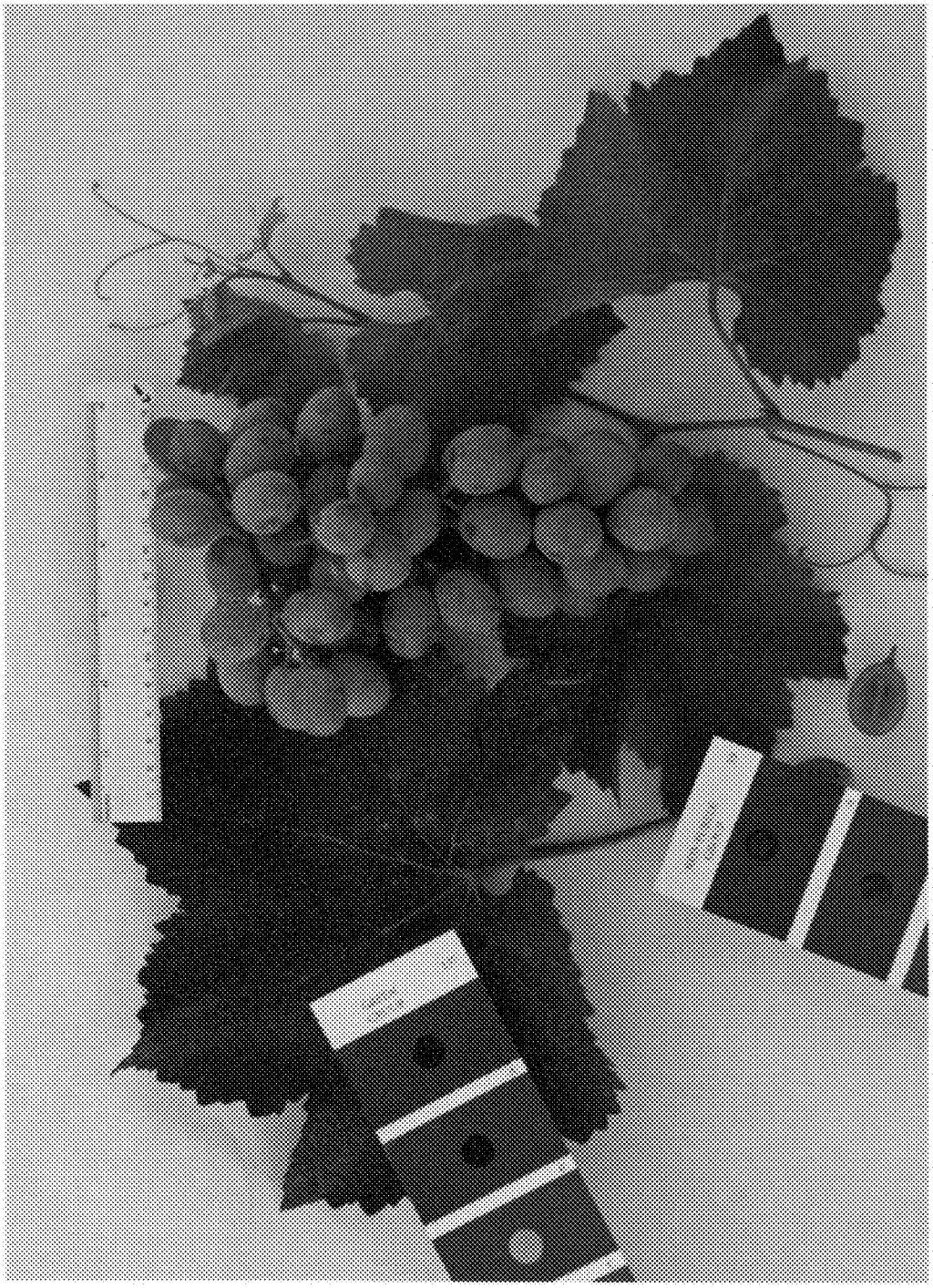

* * * * *